United States Patent

Bonnert et al.

Patent Number: 5,846,989
Date of Patent: Dec. 8, 1998

[54] BENZOTHIAZOLONE DERIVATIVES

[75] Inventors: Roger Victor Bonnert, Hoton; Roger Charles Brown, Loughborogh; Peter Alan Cage, Shepshed; Francis Ince, Loughborogh; Garry Pairaudeau, Ketton, all of United Kingdom

[73] Assignee: Astra Pharmaceuticals Limited, Herts., England

[21] Appl. No.: 776,770

[22] PCT Filed: Sep. 12, 1996

[86] PCT No.: PCT/GB96/02247

§ 371 Date: Feb. 7, 1997

§ 102(e) Date: Feb. 7, 1997

[87] PCT Pub. No.: WO97/10227

PCT Pub. Date: Mar. 20, 1997

[30] Foreign Application Priority Data

Sep. 15, 1995 [GB] United Kingdom ............ 9518952
Jul. 10, 1996 [GB] United Kingdom ............ 9614346

[51] Int. Cl.$^6$ ............ C07D 277/68; A61K 31/395
[52] U.S. Cl. ............ 514/367; 548/165; 548/166; 548/169
[58] Field of Search .................. 548/165, 166, 548/169; 514/367

[56] References Cited

FOREIGN PATENT DOCUMENTS

| 0 046 666 | 8/1981 | European Pat. Off. . |
| 0 113 964 | 11/1983 | European Pat. Off. . |
| 0 174 811 | 9/1985 | European Pat. Off. . |
| 0 175 525 | 9/1985 | European Pat. Off. . |
| 0 178 919 | 10/1985 | European Pat. Off. . |
| 0 180 994 | 11/1985 | European Pat. Off. . |
| 0 304 789 | 8/1988 | European Pat. Off. . |
| WO 92/08707 | 5/1992 | WIPO . |
| WO 93/23385 | 11/1993 | WIPO . |
| WO 93/24473 | 12/1993 | WIPO . |

OTHER PUBLICATIONS

"Synthesis and Evaluation of Non–Catechol D–1 and D–2 Dopamine Receptor Agonists: Benzimidazol–2–one, Benzoxazol–2–one, and the Hightly Potent Benzothiazol–2–one 7–Ethlamines" Joseph Weinstock et al., Journal of Chemistry, vol. 30, pp. 1166–1176.

*Primary Examiner*—Jane Fan
*Attorney, Agent, or Firm*—Nixon & Vanderhye

[57] ABSTRACT

A compound of formula I, including optical isomers thereof,

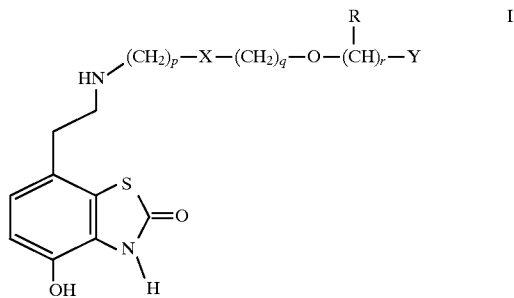

wherein

X represents —$SO_2NH$— or —$NHSO_2$—, p, q and r independently represent 2 or 3, Y represents thienyl optionally substituted by alkyl or halogen, or phenylthio- or phenyl optionally substituted by alkyl or halogen, and each R independently represents H or alkyl, and pharmaceutically acceptable salts, esters and amides thereof.

14 Claims, No Drawings

BENZOTHIAZOLONE DERIVATIVES

This application is a 371 of PCT/GB96/02247 now WO 97/10227.

1. Field of the Invention

This invention relates to novel benzothiazolone derivatives, in particular novel 7-(2-aminoethyl)-benzothiazolone derivatives, and to processes for their preparation, pharmaceutical compositions containing them and methods of treatment involving their use. The novel compounds are dopamine $DA_2$- receptor agonists and $\beta_2$-adrenoreceptor agonists.

2. Background

Benzothiazolone derivatives are known. For example, international patent applications, publication numbers WO92/08708 and WO 93/23385 disclose biologically active amines, among them biologically active aminoethyl benzothiazolone derivatives which are $\beta_2$-adrenoreceptor agonists and dopamine $DA_2$-receptor agonists, and which are indicated in the treatment of obstructive airways diseases.

WO 93/24473 discloses 7-(2-aminoethyl)-benzothiazolone compounds of formula

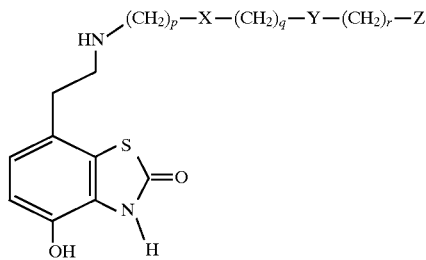

wherein X and Y are independently —S(O)$_n$— or —O—; n is 0, 1 or 2; p, q and r are independently 2 or 3; Z is phenyl optionally substituted by halogen, $OR^1$, $NO_2$ or $NR^2R^3$; or Z is a 5 or 6 membered N, O or S containing heterocycle; and $R^1$, $R^2$ and $R^3$ are independently hydrogen or alkyl $C_{1-6}$. The compounds are $\beta_2$-adrenoreceptor agonists and dopamine $DA_2$-receptor agonists, and are indicated in the treatment of obstructive airways diseases. We have now found a group of novel 7-(2-aminoethyl)-benzothiazolone derivatives which are useful as dopamine $DA_2$-receptor agonists and $\beta_2$-adrenoreceptor agonists.

OUTLINE OF THE INVENTION

Accordingly, in one aspect of the present invention there are provided compounds of formula I, including optical isomers thereof,

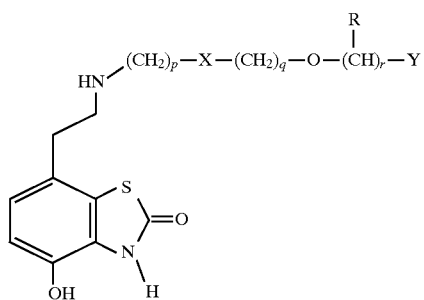

wherein

X represents —SO$_2$NH— or —NHSO$_2$—, p, q and r independently represent 2 or 3, Y represents thienyl optionally substituted by alkyl or halogen, or phenylthio- or phenyl optionally substituted by alkyl or halogen, and each R independently represents H or alkyl and pharmaceutically acceptable salts, esters and amides thereof The compounds are pharmacologically active. They show both dopamine $DA_2$-receptor agonism and $\beta_2$-adrenoreceptor agonism. They exhibit little or no $\alpha_1$-adrenoreceptor agonism. The compounds have an advantageous duration of action and $DA_2/B_2$ ratio.

Preferably, q in formula I above is 2. r is preferably 2.

When Y is phenyl substituted by alkyl, the alkyl group is preferably a $C_{1-6}$, for example a $C_1$ or $C_2$ group, most preferably methyl.

When Y is phenyl substituted by halogen, the halogen substituent is preferably a chloro- or fluoro-substituent.

Preferred compounds of the present invention are compounds of formula I wherein X is SO$_2$NH, p is 3 and q and r are each 2. Other preferred compounds are compounds of formula I wherein X is NHSO$_2$, and p, q and r are all 2.

Suitable pharmaceutically acceptable salts of the compounds of formula I include acid addition salts derived from inorganic and organic acids. The compounds may also form salts with suitable bases. Examples of suitable salts include the hydrochloride, citrate, D,L-lactate, hemisulphate, hemitatrate, D-gluconate, methanesulphonate, p-toluenesulphonate, hemifumarate, benzoate, xinafoate, hemisuccinate, 3-hydroxy-2-naphthoate, hemiembonate, hemimaleate, D-camphorsulphonate, 10-undecanoate, mandelate, naphthalene-l-sulphonate, naphthalene-2-sulphonate, 4-methoxybenzoate, 4-chlorobenzoate, 5-methylsalicylate, saccharinate, monomethyl suberate, hemisuberate and diphenyl acetate salts.

Suitable pharmaceutically acceptable esters of the compounds of formula I include phenylalkyl and alkyl esters.

Suitable amides include unsubstituted or mono- or di-substituted alkyl or phenyl amides.

The most preferred compounds of the invention are

3-[2-(4-Hydroxy-2-oxo-3H-1,3-benzothiazol-7-yl) ethylamino]-N-[2-(2-phenylethoxy)ethyl] propanesulphonamide;

N-[2-[2-(4-Hydroxy-2-oxo-3H- 1,3-benzothiazol-7-yl) ethylamino]ethyl]-2-(2-phenylethoxy) ethanesulphonamide;

3-[2-(4-Hydroxy-2-oxo-3 H-1,3-benzothiazol-7-yl) ethylamino]-N-[2-[2-(5 -methyl -2-thienyl)ethoxy]ethyl] propanesulphonamide;

N-[2-[2-(4-Fluorophenyl)ethoxy]ethyl]-3-[2-(4-hydroxy-2-oxo-3H-1,3-benzothiazol-7-yl)ethylamino] propane-sulphonamide;

N-[2-[2-(4-Chlorophenyl)ethoxy]ethyl]-3-[2-(4-hydroxy-2-oxo-3H-1,3-benzothiazol-7-yl)ethylamino] propanesulphonamide;

3-[2-(4-Hydroxy-2-oxo-3H- 1,3-benzothiazol-7-yl) ethylamino]-N-[2-[2-(4 -methylphenyl)ethoxy]ethyl] propanesulphonamide;

(R,S)-3-[2-(4-Hydroxy-2-oxo-3H-1 ,3-benzothiazol-7-yl) ethylamino]-N-[2-(2-phenyl-1-propoxy)ethyl] propanesulphonamide;

3-[2-(4-Hydroxy-2-oxo-3H-1,3-benzothiazol-7-yl) ethylamino]-N-[2-[2-(2 -methylphenyl)ethoxy]ethyl] propanesulphonamide; and 3-[2-(4-Hydroxy-2-oxo-3H-1,3-benzothiazol-7-yl) ethylamino]-N-[2-(2- phenylthioethoxy)ethyl] propanesulphonamide;

preferably in salt form and more preferably as the hydrochloride.

The present invention also provides a method for the production of compounds of formula I, comprising selective reductive alkylation of a compound of formula II,

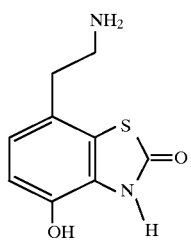

with a compound of formula III,

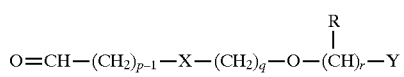

in which p, q, r, R, X and Y are as defined above, in the presence of a reducing agent.

The reducing agent may be, for example, hydrogen in the presence of a catalyst such as platinum, platinum oxide, palladium, palladium oxide, Raney nickel or rhodium, on a support e.g. charcoal, using an alcohol, e.g. ethanol, or an ester, e.g. ethyl acetate, or an ether, e.g. tetrahydrofuran, or water, as reaction solvent, or a mixture of solvents, at normal or elevated temperature and pressure. The preferred temperature is room temperature. The preferred pressure is 1–3 atmospheres. Alternatively the reducing agent may be sodium borohydride or a metal hydride e.g. sodium cyanoborohydride. Suitable solvents for use with hydride reducing agents will depend on the particular hydride used and will be well known to the person skilled in the art. Suitable solvents will include alcohols, for example ethanol or methanol.

The process may give rise to intermediate imine compounds, which may be reduced under the described conditions, to give compounds of formula I.

The compound of formula II may be prepared by known methods, for example by the method described in J. Med. Chem., 1987, 30, 1116.

Aldehydes of formula III may be prepared in a number of ways known per se. For example, isothiazolidine dioxides (as in Example 1c, for instance) may be reduced with DIBAL in toluene; acetals (as in Example 2b, for instance) may be hydrolysed with 70% aqueous acetic acid; and esters (as in Example 3d, for instance) may be reduced with DIBAL in toluene. Specific syntheses of certain precursor compounds are described in the Examples and may be adapted to a variety of targets.

The aldehydes of formula III may also be prepared from the corresponding alcohols by partial oxidation using DMSO, DCC and anhydrous phosphoric acid; or using pyridinium chlorochromate or pyridinium dithromate.

The present invention also provides a further process for preparing compounds of formula I, comprising the selective reduction of a compound of formula IV,

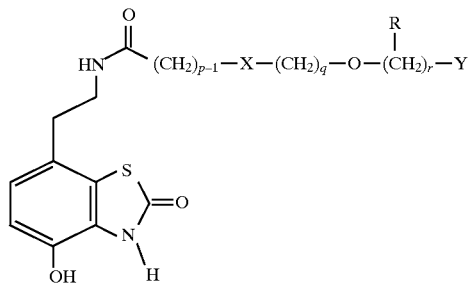

in which p, q, r, R, X and Y are as defined above.

Suitable reducing agents include electrophilic reducing agents, e.g., diborane and alane (aluminium hydride), or nucleophilic reducing agents, e.g., a complex metal hydride such as sodium bis(2-methoxyethoxy)aluminium hydride. The preferred reducing agent is diborane. The solvent should be inert to the reaction conditions. Aprotic solvents are preferred, e.g. tetrahydrofuran, diethyl ether, or 1,2-dimethoxyethane. The reaction may be carried out at a temperature of from about 0° C., to about 100° C., preferably at reflux temperature.

Compounds of formula IV may be prepared by coupling of the amine of formula II and an appropriate acid, of formula V

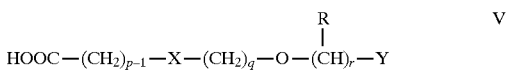

or corresponding acid chloride by conventional means. For example, the coupling may be performed in the presence of dicyclohexylcarbodiimide using the method of Sheehan and Hess, J. Am. Chem. Soc., 1955, 77, 1067; or 1,1'-carbonyldiimidazole as described by Staab, Angew. Chem. Int. Ed. Engl., 1962, 1, 351; or bromotripyrrolidinophosphonium hexafluorophosphate in a solvent such as DMF, following the procedure of Example 1e. The acids required for the process may be obtained from the corresponding esters, by hydrolysis with lithium hydroxide in aqueous methanol, following the procedure of Example 1b. Examples 1a, 2d, 3d, 4f ; 5d, 6d, 7d, 8d and 9d describe specific processes for forming the esters, and these process may be adapted to give other esters, for forming further acids for coupling with formula II amines. The acid chlorides may be prepared from the acids for example by reaction with oxalyl chloride or thionyl chloride in toluene at a temperature from ambient to reflux.

The compounds of the present invention may be prepared by several other methods as well.

Alkylation of the compound of formula II, or a salt, ester or amide thereof, with an alkylating agent of formula VI

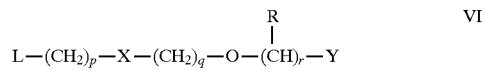

in which p, q, r, R, X and Y are as defined above and L represents a good leaving group, for example a halide e.g. chloride, bromide or iodide, or an alkyl- or aryl-sulphonyloxy group, for example methanesulphonyloxy, is one such method.

The reaction may be carried out for example in the presence of a base, for example an inorganic base, e.g., sodium or potassium carbonate, or an organic base, e.g., triethylamine, N,N'-diisopropylethylamine or pyridine.

The reaction may be performed in a solvent, for example an ether, e.g. tetrahydrofuran or dioxan, a ketone, e.g. butanone or methyl isobutyl ketone, a substituted amide, e.g. dimethylformamide, or a chlorinated hydrocarbon, e.g. chloroform, at a temperature of between ambient temperature and the reflux temperature of the solvent. Preferably the reaction is carried out at ambient temperature.

The alkylating agent of formula VI may be prepared from the corresponding alcohol (i.e. the compound in which L represents OH) by methods known to the person skilled in the art. For example, the alcohol may be reacted with a halogenating agent to yield the compound of formula VI in which L represents a halogen atom. Suitable halogenating agents include, for example, triphenylphosphine-tetrahalogenomethane adduct (conveniently formed in situ, e.g. by the reaction of triphenylphosphine and carbontetrabromide). The reaction may take place in the presence of a solvent such as acetonitrile, or a chlorinated hydrocarbon, e.g. dichloromethane, for example at a temperature in the range of 0°–30° C.

Another method is the selective reduction of a compound of formula VII,

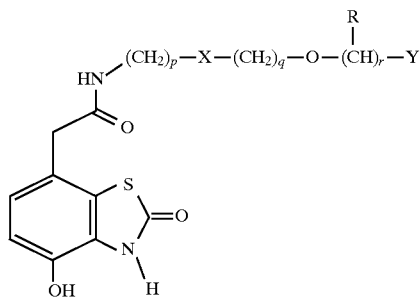

in which p, q, r, R, X and Y are as defined above.

Suitable reducing agents include electrophilic reducing agents, e.g., diborane and alane (aluminium hydride), or nucleophilic, e.g., a complex metal hydride such as sodium bis(2-methoxyethoxy)aluminium hydride. The preferred reducing agent is diborane. The solvent should be inert to the reaction conditions. Aprotic solvents are preferred, e.g. tetrahydrofuran, diethyl ether, or 1,2-dimethoxyethane. The reaction may be carried out at a temperature of from about 0° C., to about 100° C., preferably at reflux temperature.

Compounds of formula VII may be prepared by coupling of an amine and an acid or acid chloride by conventional means. For example, the coupling may be performed in the presence of dicyclohexylcarbodiimide or 1,1'-carbonyldiimidazole or bromotripyrrolidinophosphonium hexafluorophosphate, as described above in relation to compounds of formula IV. The amines required for the coupling reaction may be prepared by reaction of compounds of formula VI, where L represents a good leaving group for example a halide such as chloride or bromide, with phthalimide in the presence of a base. The resulting imides may then be treated with hydrazine hydrate in ethanol to give compounds of formula VI with the leaving group replaced by an amino group.

In the above processes it may be necessary for any functional groups. e.g. hydroxy or amino groups, present in the starting materials to be protected. Suitable protecting groups and methods for their removal are, for example, those described in "Protective Groups in Organic Synthesis" by T. W. Greene and P. G. M. Wuts, John Wiley and Sons Inc., 1991.

Another process for preparing compounds of formula I comprises removal of a protecting group from a corresponding protected compound of formula I in which one or more of the functional groups is protected, and where desired or necessary converting the resulting compound of formula I to a pharmaceutically acceptable salt, ester or amide thereof, or vice versa.

Pharmaceutically acceptable salts may be prepared for example by reacting the compound of formula I with an appropriate acid in the presence of a suitable solvent.

Pharmaceutically acceptable esters of the compounds of formula I may be made by conventional techniques, e.g. esterification or transesterification.

Pharmaceutically acceptable amides of the compounds of formula I may be made by conventional techniques, e.g. reaction of a compound of formula I with an acid or acid chloride.

The intermediates of formula IV are novel, thus according to a further aspect of the invention there are provided compounds of formula IV,

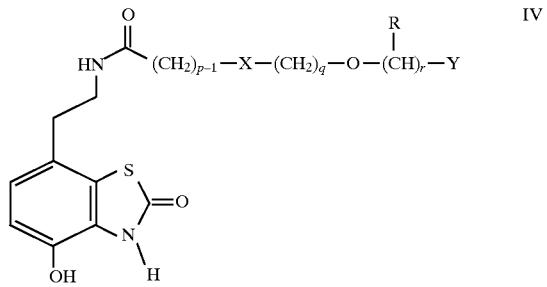

in which p, q, r, R, X and Y are as defined above.

The intermediates of formula VII as defined above are also novel and are thus also provided in accordance with the present invention.

Further, the aldehydes of formula III as defined above are novel and are provided by the present invention.

Still further the acids of formula V and corresponding acid chlorides are novel and are provided by the present invention.

The compounds of formula I and salts, esters and amides thereof are dopamine $DA_2$-receptor agonists. The binding affinities of the test compounds for the $DA_2$ receptor binding sites in bovine pituitary membranes may be determined from the displacement of [$^3$H]-N-n-propylnorapomorphine and of [$^3$H]-spiperone in the absence or presence of nonhydrolysable GTP analogue respectively, D. R. Sibley, A. DeLean and I. Creese, Anterior Pituitary Dopamine Receptors, Demonstration of Interconvertible High and Low Affinity States of the D-2 Dopamine Receptor, J. Biol. Chem., 1982, 257(11), 6351–6361. The $DA_2$-receptor activity may also be demonstrated in a functional screen, the rabbit isolated ear artery, as described by Brown and O'Connor, Br. J. Pharmacol., 1981, 73, 189P. The compounds are also $\beta_2$-adrenoreceptor agonists. This activity may be demonstrated in the isolated trachea of the guinea pig, as described by I. G. Dougall, D. Harper, D. M. Jackson, and P. Leff, Br. J. Pharmacol., 1991, 104, 1057. $\alpha_1$-Receptor activity may be analysed using the rabbit isolated ear artery screen described in Pharmacological Example herein.

The compounds of formula I and salts, esters and amides thereof are thus indicated for use in the treatment of the range of airways diseases, including conditions such as asthma, including bronchial asthma, allergic asthma, intrinsic asthma (for example late asthma and airway hyperresponsiveness); and bronchitis and the like (see, for example, UK Patent No. 2022078 and Br. J. Pharmacol., 1987, 24, 4983).

The compounds of formula I and salts, esters and amides thereof are also indicated for use in the treatment of various other conditions, e.g. inflammatory and allergic skin disorders, cancer e.g. small cell lung cancer, congestive heart failure and glaucoma.

The term "treatment" as used herein includes prophylaxis as well as relief of the symptoms of disease.

Accordingly, in a further aspect of the present invention, there is provided the use of a compound of formula I, or a pharmaceutically acceptable salt, ester or amide thereof, in therapy.

Further, there is provided the use of a compound of formula L or a pharmaceutically acceptable salt, ester or amide thereof, in the manufacture of a medicament for the treatment of obstructive airways disease, in particular for the treatment of asthma or chronic bronchitis.

Still further, the present invention provides a method of treatment of airways disease, which method comprises administering a therapeutically effective quantity of a compound of formula I, or a pharmaceutically acceptable salt, ester or amide thereof, to a patient suffering from or susceptible to such a condition.

Typical daily unit doses may be for example 1 $\mu$g–10 mg for topical administration, preferably 10–500 $\mu$g, for example divided two or three times, or 10 $\mu$g–100 mg for oral administration, preferably 100 $\mu$g–10 mg, for example divided two or three times.

The compounds of formula I and salts, esters and amides thereof may be used on their own or in the form of appropriate pharmaceutical compositions.

Administration may be by inhalation as well as by other routes, for example by oral or intraveneous administration.

Nasal or pulmonary administration may be achieved via a suitable inhalation device.

For example metered dose inhaler devices may be used to administer the compound, dispersed in a suitable propellant and with or without additional excipients such as ethanol, surfactants, lubricants and stabilising agents.

Suitable propellants include hydrocarbon, chlorofluorocarbon and hydrofluoroalkane propellants, or mixtures of any such propellants. Especially preferred propellants are P134a and P227 each of which may be used alone or in combination with other propellants and/or surfactants and/or other excipients, for example in combination with each other.

Nebulised aqueous suspensions or, preferably, solutions may also be employed, with or without a suitable pH and/or tonicity adjustment, either as a unit-dose or multi-dose device.

Dry powder inhalers may be used to administer the compound, alone or in combination with a pharmaceutically acceptable carrier, in the latter case either as a finely divided powder or as an ordered mixture. The dry powder inhaler may be single dose or multi-dose and may utilise a dry powder or a powder-containing capsule.

Metered dose inhaler, nebuliser and dry powder inhaler devices are well known and a variety of such devices are available.

The invention is illustrated, but in no way limited, by the following Examples, in which temperatures are in degrees Celsius. Where necessary, the reactions were performed under an inert atmosphere of either nitrogen or argon. Where necessary, preparative HPLC separations were generally performed using a Novapak®, Bondapak® or Hypersil® column packed with BDSC-18 reverse phase silica. Flash chromatography was carried out using Fisher Matrix 60 silica, 35–70 micron.

EXAMPLE 1

3-[2-(4-Hydroxy-2-oxo-3H-1,3-benzothiazol-7-yl) ethylamino]-N-[2 -(2-phenylethoxy)ethyl] propanesulphonamide hydrochloride a) Methyl 3-[2-(2-phenylethoxy)ethylaminosulphonyl] propanoate 2-(2-Phenylethoxy)ethanamine[1] (1.95 g) was stirred in dichloromethane at room temperature. Triethylamine (3.36 ml) followed by methyl 3-(chlorosulphonyl)-propanoate[2] were added and the mixture stirred overnight at room temperature. The mixture was diluted with a further amount of dichloromethane, washed with dilute hydrochloric acid then water, then dried ($MgSO_4$). The solvent was removed in vacuo to yield a pale yellow oil which was further purified by flash chromatography (01% ethanol:dichloromethane as eluant) to give the subtitle compound as pale yellow oil (1.68 g).

[1]Chem. Ber., 1964, 97, 510–519.
[2]J. Am. Chem. Soc., 1950, 72, 128–132.

Mass spectrum: FAB 316 (M+H);
$^1$H nmr (360 MHz, $CDCl_3$)$\delta$:2.75 (2H, t), 2.85 (2H, t), 3.18–3.35 (4H, m), 3.46–3.57(2H, m), 3.60–3.77 (5H, m), 4.44 (1H, brt), 7.12–7.35 (5H, m).

b) 3-[2-(2-Phenylethoxy)ethylaminosulphonyl]propanoic acid

The product of step a) (1.68 g) was dissolved in methanol (30 ml). Lithium hydroxide (0.45 g) in water (30 ml) was added and the mixture stirred overnight at room temperature. Water was added and the mixture washed with ether. The aqueous layer was acidified with dilute hydrochloric acid and extracted with ether. The ether extract was washed with water then brine, then dried ($MgSO_4$). The solvent was removed in vacuo to give the subtitle compound as a white solid (0.97 g) which was used without further purification.

mp 80°–82°;
Mass spectrum: ESI 300 (M–H);
$^1$H nmr (360 MHz, $CDCl_3$$\delta$: 2.77–2.95 (4H, m), 3.20–3.47 (4H, m), 3.51–3.58 (2H, m), 3.69 (2H, t), 4.66 (1H, t); 7.18–7.38 (5H, m).

c) 2-[2-(2-Phenylethoxy)ethyl]-3-isothiazolidinone-1,1'-dioxide

The product of step b) (34 g) was dissolved in dimethylformamide (200 ml). To this stirred solution was added 1,1'-carbonyldiimidazole (20.12 g) and the mixture stirred for 2 hours. Triethylamine (15.7 ml) was added and the mixture was stirred at room temperature for 60 hours. The mixture was poured into dilute hydrochloric acid and extracted with ethyl acetate (×3). The combined organic extracts were washed with saturated sodium bicarbonate solution then brine, dried ($MgSO_4$) and the solvent removed in vacuo to yield a pale yellow oil which was further purified by flash chromatography (50% ethyl acetate:petrol as eluant) to give the subtitle compound as an oil (27.4 g).

Mass spectrum: ESI 301 (M+$NH_4$);
$^1$H nmr (360 MHz, $CDl_3$) $\delta$: 2.87 (2H, t), 2.99 (2H, t) 3.51 (2H, t), 3.64–3.68 (4H, m),3.76 (2H, t), 7.18–7.43 (5H, m).

d) 3-[2-(4-Hydroxy-2-oxo-3H-1,3-benzothiazol-7-yl) ethylamino]-N-[2-(2 -phenylethoxy)ethyl] propanesulphonamide hydrochloride The product of step c) (0.62 g) was stirred in toluene (20 ml) then cooled to –70° C. Diisobutylaluminium hydride (1.6 ml of a 1.5M solution in toluene) was added over 15 min keeping the temperature below –58°. The mixture was stirred for 10 min after which time tlc showed that no starting material remained. Ethyl acetate (9 ml) was cautiously added keeping the temperature below –60°. The mixture was allowed to warm to room temperature and a 10% aqueous solution of sodium potassium tartrate added. After stirring for 1 hour the mixture was extracted with ethyl acetate (×3). The combined organic extracts were dried ($MgSO_4$) and then about 70% of the solvent was removed in vacuo. Methanol (20 ml) was added to the mixture and again about 70% of the solvent was removed in vacuo, this was repeated twice more. This solution was diluted with methanol (20 ml) and 7-(2-aminoethyl)-4-hydroxy-1,3-benzothiazol-2(3H)-one hydrobromide (0.64 g) added. The pH was adjusted to pH 4 with glacial acetic acid. Sodium cyanoborohydride (0.14 g) was added followed by sodium sulphate (50 mg) and the mixture stirred for 72 hours. The mixture was made basic by the addition of concentrated aqueous ammonium hydroxide solution. The volatiles were remove in vacuo and the residue purified by flash chromatography (10–25% methanol in chloroform as eluant). The material was further purified by reverse phase HPLC (25% methanol in 0.1% aqueous trifluoroacetic acid as eluant) to give, after conversion to the hydrochloride salt, the title compound as a white solid (0.417 g).

mp 205–206°;
Mass spectrum: FAB 480 (M+H);
$^1$H nmr (360 MHz, d$_6$DMSO) δ:2.00 (2H, t), 2.73–2.92 (4H, m), 2.96–3.19 (8H, m), 3.44 (2H, t), 3.60 (2H, t), 6.75 (1H, d), 6.85 (1H, d), 7.13–7.35 (6 H, m), 8.92 (2H, s) 10.41 (1H, s), 11.77 (1H, s);
Analysis Found: C,51.48; H,6.25; N,8.41; S, 12.50% Required for C$_{22}$H$_{29}$N$_3$O$_5$S$_2$.HCl: C,51.20; H,5.86; N,8.14; S,12.43%

In an alternative method, steps a) and b) above were repeated, followed by steps e) and f) below:

e) N-[2-(4-Hydroxy-2-oxo-3H-1,3-benzothiazol-7-yl)ethyl]-3-[2-(2 -phenylethoxy)ethylaminosulphonyl]propanamide A solution of the product from step b) (3.89 g), 7-(2-aminoethyl)-4-hydroxy-1,3 -benzothiazol-2(3H)-one hydrochloride (3.22 g), bromotripyrrolidinophosphonium hexafluorophosphate, PyBroP, (6.32 g) in dimethylformamide (50 ml) was cooled to –15° C. and diisopropylethylamine (9.0 ml) was added dropwise over 5 minutes. The solution was stirred at –15° C. for 5 min then allowed to warm to 13° C. over 4 hours. This mixture was then added dropwise over 40 min to dilute hydrochloric acid (2N, 500 ml) and after stirring over the weekend the solid was collected by filtration. This solid was dried in vacuo to give the subtitle compound (4.5 g).

Mass spectrum FAB 492 (M–H).

f) 3-[2-(4-Hydroxy-2-oxo-3H-1,3-benzothiazol-7-yl) ethylamino]-N-[2-(2 -phenylethoxy)ethyl] propanesulphonamide hydrochloride To a solution of the product from step e) (0.28 g) in tetrahydrofuran (2 ml) was added borane tetrahydrofuran (2.44 ml of 1M solution) over 5 min. The mixture was heated at reflux for 3 hours and, after cooling, methanol (1 ml) was added cautiously. The volatiles were removed in vacuo, the residue was redissolved in methanol (5 ml) and concentrated hydrochloric acid (1 ml) was added. The volatiles were again removed in vacuo. The residue was partitioned between water and ethyl acetate, the aqueous layer collected and extracted again with ethyl acetate. The aqueous layer was then made basic with sodium hydrogen carbonate and extracted four times with chloroform. The combined chloroform extracts were dried and the volatiles removed in vacuo to provide after conversion to the hydrochloride salt, the title compound (0.070 g).

EXAMPLE 2

N-[2-[2-(4-Hydroxy-2-oxo-3H-1,3-benzothiazol-7-yl)ethylamino]ethyl]-2-(2 -phenylethoxy) ethanesulphonamide hydrochloride a) 2-(2-Phenylethoxy)ethanesulphonylchloride A stirred suspension of 2-(2-phenylethoxy)ethanethiol (1.0 g) in water (40 ml) was saturated at 5°–10° with chlorine over 20 min. The mixture was flushed under a stream of nitrogen to remove any excess chlorine. The mixture was then extracted with dichloromethane (×2), the combined organic extracts were washed with water then dried (CaCl$_2$). The solvent was removed in vacuo to give an oil which was azeotroped with toluene to give the subtitle compound as a yellow oil (1.36 g) which was used without further purification.

Mass spectrum: EI 248/250 (M);
$^1$H nmr (360 MHz, CDCl$_3$) δ: 2.90 (2H, t), 3.74 (2H, t), 3.88 (2H, t), 3.99 (2H, t), 7.13–7.36 (5H, m).

b) N-(2,2-Dimethoxyethyl)-2-(2-phenylethoxy) ethanesulphonamide

A stirred solution of the product of step a) (1.0 g) in dichloromethane (20 ml) and pyridine (0.358 ml) was treated dropwise over 5 min with a solution of aminoacetaldehyde dimethylacetal (0.438 ml) in dichloromethane (5 ml). The mixture was stirred at room temperature for 2 days. The mixture was washed with water then dried (CaCl$_2$). The volatiles were removed in vacuo to yield an orange oil which was further purified by flash chromatography (ether as eluant) to give the subtitle compound as a yellow oil (0.42 g).

Mass spectrum: 335 (M+NH$_4$);
$^1$H nmr (360 MHz, CDCl$_3$) δ: 2.90 (2H, t), 3.13 (2H, t) 3.26 (2H, t), 3.38 (6H, m). 3.73 (2H, t), 3.85 (2H, t), 4.38 (1H, t), 4.46 (1H, t), 7.14–7.35 (5H, m).

N-[2-(2-(4-Hydroxy-2-oxo-3H-1,3-benzothiazol-7-yl) ethylamino)ethyl]-2-(2-phenylethoxy)ethanesulphonamide hydrochloride A solution of the product of step b) (0.26 g) in 70% aqueous acetic acid (5 ml) was heated to 100° for 2 hours after which time tlc indicated that no starting material remained. The solvent was removed in vacuo. The residue was taken up into methanol (10 ml) and to this stirred solution was added 7-(2-aminoethyl)-4-hydroxy-1,3-benzothiazol-2(3H)-one hydrobromide (0.238 g), sodium cyanoborohydride (0.038 g) followed by acetic acid (1 drop). The mixture was stirred at room temperature for 24 hours. The mixture was made basic by the addition of concentrated aqueous ammonium hydroxide solution. The volatiles were removed in vacuo and the residual material purified by flash chromatography (17% ethanol in dichloromethane as eluant) to give a light yellow gum. This was further purified by reverse phase HPLC (30–45% acetonitrile in 0.1% aqueous trifluoroacetic acid as eluant) to give, after conversion to the hydrochloride salt, the title compound as a white powder (0.080 g).

Mass spectrum: 466 (M+H);
$^1$H nmr (360 MHz, d$_6$DMSO) δ: 2.81–2.90 (4H, m), 3.04–3.09 (4H, brd), 3.26–3.28 (2H, m), 3.24 (2H +H$_2$O), 3.63 (2H, s), 3.74 (2H,t), 6.78 (1H,d), 6.87 (1H,d),719–7.30 (5H, m), 7.43 (1H, t), 9.10 (2H,s), 10.16 (1H s), 11.78 (1H, s);
Analysis Found: C,49.35; H,5.69; N,8.30; S, 11.94% Required for C$_{21}$H$_{27}$N$_3$O$_5$S$_2$.HCl.0.5 H$_2$O: C,49.31; H,5.67; N,8.22; S,12.52 %

In an alternative method, step a) was repeated, followed by steps d) to g) below:

d) Methyl [2-(2-phenylethoxy)ethylsulphonylamino]acetate

A suspension of glycine methylester hydrochloride (2.52 g) in dichloromethane (30 ml) was stirred at –18° C. and diisopropylethyl amine (8 ml) was added over 10 min. To this was added the product from part a) (2.64 g) in dichloromethane (10 ml) dropwise over 10 minutes keeping the temperature below –5° C. The cooling bath was removed and the stirred mixture allowed to warm to room temperature. After a further 50 minutes the mixture was washed with 5% aqueous potassium hydrogen sulphate the dried (Na$_2$SO$_4$) and the volatiles removed in vacuo to give the subtitle compound as a brown oil (58.5 g).

Mass spectrum FAB 302 ( M+H)
$^1$H nmr (360 MHz, CDCL$_3$): 2.90 (2H, t), 3.36 (2H, t), 3.72–3.85 (7H, m), 3.96 (2H, t), 4.70 (1H, brs), 7.20–7.31 (5H, m).

e) 2-[(2-Phenylethoxy)ethylsulphonylamino]acetic acid

A solution of the product from part d) (3.2 g) in methanol (30 ml) was cooled in an ice bath and treated with a solution of lithium hydroxide.hydrate (1.06 g) in water (7 ml) over 5 minutes. The cooling bath was removed and the mixture stirred for 16 hours. The mixture was acidified with concentrated hydrochloric acid (3 ml) and then concentrated in vacuo to approximately 15 ml. The residue was mixed with sodium bicarbonate and extracted with ether. The aqueous phase was then reacidified with saturated aqueous potassium hydrogen sulphate solution and extracted with ether. This extract was dried (MgSO$_4$) and volatiles removed in vacuo to give a solid. The product was further purified by recrystallization from dichloroethane-toluene mixture to give the subtitle compound as a crystalline solid (1.57 g).

Mass spectrum FAB 288 (M+H);
$^1$H nmr (360 MHz, CDCL$_3$): 2.90 (2H, t), 3.32 (2H, t), 3.74–3.78 (4H, m), 3.89 (2H, t), 4.66 (1H, t), 7.20–7.33 (5H, m), 8.07 (1H, brs).

f) N-[2-(4-Hydroxy-2-oxo-3H-1,3-benzothiazol-7-yl)ethyl]-2-[2-(2 -phenylethoxy)ethylsulphonylamino]acetamide A solution of the product from part e) (70 g) in dimethylformamide (605 ml) was cooled to −10° C. and 1,1'-carbonyldiimidazole (39.5 g) was added. The mixture was stirred for 119 minutes then 7-(2-aminoethyl)4-hydroxy-1,3-benzothiazol-2(3H)-one hydrochloride (68.87 g) was added followed by triethylamine (34 ml) drop wise over 3 minutes keeping the temperature at −10° C. After a further 10 minutes at −10° C. the mixture was allowed to warm to room temperature and stirred for 24 hours. This mixture was then added dropwise to dilute hydrochloric acid (2N, 1870 ml) and aqueous mixture was extracted with ethyl acetate. The organics were then washed with dilute hydrochloric acid, aqueous sodium bicarbonate and then dried (MgSO$_4$). The volatiles were removed in vacuo to provide the subtitle compound as a foam (92.21 g).

Mass spectrum FAB 480 (M+H);
$^1$H nmr (360 MHz, d$_6$DMSO): 2.61 (2H, t), 2.81 (2H, t), 3.29–3.32 (4H, m overlapping water), 3.56 (2H, s), 3.61 (2H, t), 3.74 (2H, t), 6.70 (1H, d), 6.80 (1H, d), 7.16–7.53 (5H, m), 8.03 (1H, brt).

g) N-[2-(2-(4-Hydroxy-2-oxo-3H-1,3-benzothiazol-7-yl)ethylamino)ethyl]-2-(2 -phenylethoxy)ethanesulphonamide hydrochloride A solution of the product from part f) (38.7 g) in tetrahydrofuran (200 ml) was cooled in an acetone/ice bath and lithium borohydride (727 ml, 2.0M in tetrahydrofuran) was added over 30 minutes. After 15 minutes the cooling bath was removed and trimethylsilyl chloride (205 ml) was added and the stirring continued for 162 hours at room temperature. The mixture was cooled to −20° C. and methanol carefully added. After this addition a further 50 ml of methanol saturated with hydrogen chloride was added and the mixture allowed to warm to room temperature. After 1 hour the mixture was heated at reflux for 30 minutes then cooled and the volatiles were removed in vacuo. Water (400 ml) was added and the flask thoroughly shaken and, after standing in an acetone/ice bath for 30 minutes, the water was decanted off. A further amount of water was added (100 ml) and the process repeated. The semi solid remaining was then dissolved in hot ethanol (40 ml), treated with activated charcoal (3 g) and stirred for 1 hour. The mixture was filtered and the solvent removed in vacuo. The residue was redissolved in hot ethanol (80 ml) and allowed to stand at room temperature for 16 hours. The crystals that had precipitated out were then loosened and broken up with a spatula, swirled and left to stand for a further 16 hours. The solid was then collected by filtration and washed with ethanol, ether then dried under vacuum to provide the title compound (23 g).

EXAMPLE 3

3-[2-(4-Hydroxy-2-oxo-3H-1,3-benzothiazol-7-yl) ethylamino]-N-[2-[2-(5 -methyl-2-thienyl)ethoxy] ethyl]propanesulphonamide hydrochloride a) 2-[2-(5-Methyl-2-thienyl)ethoxy]acetic acid Sodium hydride (0.622 g) was suspended in dry dimethylformamide (5 ml) and treated dropwise with a solution of 2-(5-methyl-2-thienyl)ethanol (1.0 g) in dry dimethylformamide (5 ml). The mixture was stirred at room temperature under nitrogen for 2 hours then a solution of chloroacetic acid (0.664 g) in dry dimethylformamide (5 ml) added. The mixture was stirred at room temperature overnight. The volatiles were removed in vacuo and the residue quenched with water and extracted with ethyl acetate. The aqueous layer was adjusted to pH 2 using dilute hydrochloric acid and then extracted with ethyl acetate. This extract was washed with water, brine then dried (MgSO$_4$). The solvent was removed in vacuo to give a brown oil (1.51 g) which was used without further purification.

Mass spectrum: 200 (M);
$^1$H nmr (360 MHz, CDCl$_3$) δ: 2.45 (3H, s), 3.05–3.09 (2H, t), 3.75–3.83 (2H, t), 4.17 (2H, s), 6.56 (1H, d), 6.63 (1H, d).

b) 2-[2-(5-Methyl-2-thienyl)ethoxy]acetamide

The product of step a) (6.48 g) was dissolved in toluene (55 ml) and oxalyl chloride (2.877 ml) added dropwise at room temperature under nitrogen. A drop of dimethylformamide was added and the mixture stirred for 3 hours after which time tlc showed no starting material. The volatiles were removed in vacuo to provide a brown oil (6.7 g) which was added dropwise to a stirred solution of concentrated ammonium hydroxide (50 ml) at 0°. The mixture was allowed to warm to room temperature and stirred for 4 hours. A brown solid precipitated out. This solid was collected by filtration and washed with water to give the subtitle compound (2.02 g).

Mass spectrum: 200 (M+H);
$^1$H nmr (360 MHz, CDCl$_3$) δ: 2.45 (3H s), 3.04 (2H, t), 3.73 (2H, t), 3.97 (2H, s), 5.61 (2H, brs), 6.57 (1H, d), 6.63 (1H, d).

c) 2-[2-(5-Methyl-2-thienyl)ethoxyl]ethanamine

Borane-tetrahydrofuran solution (1.0M in THF, 21.7 ml) was added dropwise to a stirred solution of the product from step b) (1.25 g) in dry tetrahydrofuran (100 ml). The reaction was heated at reflux under an inert atmosphere for 5 hours. The reaction was cooled and methanol (10 ml) added cautiously. The solvents were removed in vacuo and the residue dissolved in methanol (100 ml) to which was added concentrated hydrochloric acid (sg. 1.18, 0.45 ml). This solution was heated at reflux for 15 min then the solvent removed in vacuo. The residue was purified by flash chromatography (dichloromethane: 5% methanol as eluant) to give the subtitle compound as a white solid (0.916 g).

Mass spectrum: 186 (M+H);
$^1$H nmr (360 MHz, CDCl$_3$) δ: 2.45 (3H), s), 3.04 (2H, t), 3.73 (2H, t), 3.97 (2H, s), 5.61 (2H, brs), 6.57 (1H, d), 6.63 (1H, d).

d) Methyl 3-[2-[2-(5-methyl-2-thienyl)ethoxy] ethylaminosulphonyl]propanoate

The product of step c) as the hydrochloride salt (1.50 g) was stirred under nitrogen in dichloromethane (25 ml). Triethylamine (2.21 ml) was added followed by methyl 3-(chlorosulphonyl)propanoate (1.18 g). The mixture was stirred at room temperature overnight. The solution was diluted with a further amount of dichloromethane and the organics washed with dilute hydrochloric acid then water, then dried (MgSO$_4$). The mixture was filtered and the volatiles removed in vacuo to give the subtitle compound as an oil (1.4 g).

Mass spectrum: 336 (M+H);

$^1$H nmr (360 MHz, CDCL$_3$) δ: 2.38 (3H, s), 2.80 (2H, t), 3.00 (2H, t), 3.26 –3.36 (4H, m), 3.56 (2H, t), 3.64 (2H, t), 3.72 (3H, s), 4.71 (1H, t), 6.57 (1H, d), 6.60 (1H, d).

e) 3-[2-(4-Hydroxy-2-oxo-3H-1,3-benzothiazol-7-yl) ethylamino]-N-[2-[2-(5 -methyl-2-thienyl)ethoxy]ethyl] propanesulphonamide hydrochloride The product of step d) (0.60 g) was dissolved in toluene (30 ml) under nitrogen and cooled to −78°. Diisobutylaluminiumhydride (1.5M in toluene, 1.78 ml) was added dropwise and the mixture kept at −78° for 10 min. The reaction was quenched with ethyl acetate followed by a 10% aqueous sodium potassium tartrate solution. The mixture was warmed to room temperature and after stirring for 1 hour extracted with toluene (×3). The combined organic extracts were washed with water, dried (MgSO$_4$) then about 70% of the solvent removed in vacuo. Methanol (20 ml) was added to the mixture and again about 70% of the solvent removed in vacuo, this was repeated twice more. This solution was diluted with methanol (20 ml) and 7-(2-aminoethyl) -4-hydroxy-1,3 -benzothiazol-2(3H)-one hydrochloride (0.516 g) added. The pH was adjusted to pH 4 with glacial acetic acid. Sodium cyanoborohydride (0.114 g) was added and the mixture stirred under nitrogen for 2 hours. The mixture was made basic by the addition of concentrated aqueous ammonium hydroxide solution. The volatiles were removed in vacuo and the residue purified by flash chromatography (5–20% methanol:dichloromethane as eluant). The material was further purified by reverse phase HPLC (25–85% methanol in 0.1% aqueous trifluoroacetic acid as eluant) to give, after conversion to the hydrochloride salt, the title compound (0.12 g) as a white solid.

mp 210–212°;

Mass spectrum: FAB 500 (M+H);

$^1$H nmr (360 MHz, d$_6$DMSO) δ: 2.00 (2H, q, 2.37 (3H, s), 2.85 (2H, t), 2.93 (2H, t), 3.01–3.17 (8H, m), 3.46 (2H, t), 3.58 (2H, t), 6.60 (1H, d), 6.65 (1H, d), 6.75–6.88 (2H, m), 7.31 (1H, t), 8.93 (2H, s), 10.15 (1H, s), 11.7 (1H, brs).

EXAMPLE 4

N-[2-[2-(4-Fluorophenyl)ethoxy]ethyl]-3-[2-(4-hydroxy-2-oxo-3H-1,3-benzothiazol-7-yl) ethylamino]propanesulphonamide hydrochloride a) t-Butyl 3-[2-(4-fluorophenyl)ethoxy]propanoate 2-(4-Fluorophenyl)ethanol (20.5 g) and Triton-B (2.4 ml, 40% in methanol) were mixed together and the methanol removed in vacuo t-Butyl acrylate (21.38 ml) was added and the solution heated at 50° for 2 hours then stirred at room temperature overnight. The mixture was diluted with water and extracted with diethyl ether. The combined organic extracts were washed with brine, dried (MgSO$_4$) and filtered. The volatiles were removed in vacuo to give the subtitle compound (37.91 g) which was used without further purification.

$^1$H nmr (360 MHz, CDCl$_3$) δ: 1.46 (9H, s), 2.47 (2H, t), 2.84 (2H, t), 3.55–3.69 (4H, m), 6.93–6.98 (2H, m), 7.15–7.18 (2H, m).

b) 3-[2-(4-Fluorophenyl)ethoxy]propanoic acid

The product of step a) (37.91 g) was dissolved in dichloromethane (50 ml) and trifluoroacetic acid (50 ml) added. The solution was stirred at room temperature for 1 hour then diluted with water and extracted with ethyl acetate (×4). The combined organic extracts were washed with water (×4) then brine, dried (MgSO$_4$) and filtered. The volatiles were removed in vacuo to give an oil, this oil was taken into diethyl ether and extracted with aqueous sodium bicarbonate solution (×3). The combined aqueous layers were acidified with concentrated hydrochloric acid then extracted with diethyl ether ×4). The combined organic extracts were washed with brine, dried (MgSO$_4$) and filtered. The volatiles were removed in vacuo to give the subtitle compound (19.95 g) which was used without further purification.

Mass spectrum: 212 (M);

$^1$H nmr (360 MHz, CDCl$_3$) δ: 2.62 (2H, t), 2.85. (2H, t) 3.66 (2H, t), 3.73 (2H, t), 6.94–6.99 (2H m), 7.14–7.18 (2H, m), 7.37 (1H, brs).

c) 2-[2-(4-Fluorophenyl)ethoxy]ethylisocyanate

The product of step b) (15.49 g), triethylamine (11.2 ml) and diphenylphosphoryl azide (15.7 ml) were heated in toluene (150 ml) at 80° for 5 hours under nitrogen. The mixture was allowed to cool, then left at room temperature overnight. The mixture was diluted with water and extracted with ethyl acetate (×3). The combined organic extracts were washed with aqueous sodium bicarbonate, dilute hydrochloric acid, brine then dried (MgSO$_4$) and filtered. The volatiles were removed in vacuo and the residue further purified by flash chromatography (50% diethyl ether:iso-hexane as eluant) to give the subtitle compound (5.54 g).

Mass spectrum: 209 (M);

$^1$H nmr (360 MHz, CDCl$_3$) δ: 2.89 (2H, t), 3.38 (2H, t), 3.56 (2H, t), 3.68 (2H, t), 6.95–7.01 (2H, m), 7.17–7.21 (2H, m).

d) Methyl N- [2-(2-(4-fluorophenyl)ethoxy)ethyl]carbamate

The product of step c) (9.0 g) was dissolved in methanol (300 ml) and to this stirred solution was added sodium methoxide (4.65 g). The mixture was stirred at room temperature for 3 hours. The volatiles were removed in vacuo and the residue was extracted with ethyl acetate. The ethyl acetate was washed with brine, dried (MgSO$_4$) and filtered. The volatiles were removed in vacuo and a portion of the residue was further purified by flash chromatography (60% diethyl ether: iso-hexane as eluant) to give the subtitle compound (0.375 g).

Mass spectrum; FAB 242 (M+H);

$^1$H nmr (360 MHz, CDCl$_3$) δ: 2.84 (2H, t), 3.34 (2H, t), 3.49 (2H, t), 3.63 (2H, t), 3.67 (3H, s), 6.95–7.00 (2H, m), 7.14–7.18 (2H, m);

Analysis Found: C,59.1; H6.83; N,5.83% Required for C$_{12}$H$_{16}$FNO$_3$: C,59.74; H,6.68; N,5.81%.

e) 2-[2-(4-Fluorophenyl)ethoxy]ethanamine

The product of step d) (8.0 g) was dissolved in ethylene glycol and to this was added potassium hydroxide (48 g) and hydrazine hydrate (8.3 ml). The stirred mixture was heated to 140° for 4 hours then allowed to cool to room temperature overnight. The mixture was then diluted with water and extracted with diethyl ether (×3). The combined organic extracts were washed with brine, dried (MgOS$_4$) and filtered. The volatiles were removed in vacuo to give the subtitle compound (5.36 g).

Mass spectrum: 184 (M+H);

$^1$H nmr (360 MHz, CDCl$_3$) δ: 2.82–2.88 (4H, m), 3.47 (2H, t), 3.64 (2H, t), 6.95–6.99 (2H, m), 7.16–7.20 (2H, m).

f) Methyl 3-[2-[2-(4-fluropheny)ethoxy] ethylaminosulphonyl]propanoate

The subtitle compound (8.32 g) was prepared according to the method of Example 3d) using 2-[2-(4-fluorophenyl) ethoxy]ethanamine (5.36 g), triethylamine (4.6 ml) and methyl 3-(chlorosulphonyl)propanoate (5.6 g) in diethyl ether (150 ml).

mp 49°;

Mass spectrum: 334 (M+H);

$^1$H nmr (360 MHz, CDCl$_3$) δ: 2.78–2.87 (4H, m), 3.24–3.28 (2H, m), 3.34 (2H, t), 3.51–3.56 (2H, m), 3.65 (2H, t), 3.73 (3H, s), 6.97–7.01 (2H, m), 7.15 –7.19 (2H, m);

Analysis Found: C,50.52; H,6.24; N,4.16; S,9.40%
Required for $C_{14}H_{20}FNO_5S$: C,50.44; H,6.05; N,4.20; S,9.62%.

g) N-[2-[2-(4-Fluorophenyl)ethoxy]ethyl]-3-[2-(4-hydroxy-2-oxo-3H-1,3-benzothiazol-7-yl)ethylamino]propanesulphonamide hydrochloride The title compound (0.092 g) was prepared according to the method of Example 3e) using methyl 3-[2-[2-(4-fluorophenyl)ethoxy]ethylaminosulphonyl]propanoate (1.0 g), diisobutylaluminiumhydride (1.5M in toluene, 4 ml), 7-(2-aminoethyl)-4-hydroxy-1,3-benzothiazol-2-(3H)-one hydrochloride (0.875 g) and sodium cyanoborohydride (0.354 g).

mp 195°–7°;
Mass spectrum: FAB 498 (M+H);
$^1$H nmr (360 MHz, $d_6$DMSO) δ: 1.99 (2H, q), 2.78–2.87 (4H, m) 3.04–3.16 (8H, m), 3.45 (2H, t), 3.59 (2H, t), 6.86 (1H, d), 6.85 (1H, d), 7.01 (2H, t), 7.26–7.31 (3H, m), 8.90 (2H, s), 10.15 (1H, s), 11.77 (1H, brs);
Analysis Found: C,49.01; H,5.74; N,7.96; S,11.50%
Required for $C_{22}H_{29}FN_3O_5S_2$. HCl.0.5 $H_2O$: C,49.48; H,5.47; N,7.87; S, 12.01%.

EXAMPLE 5

N-[2-[2-(4-Chlorophenyl)ethoxy]ethyl]-3-[2-(4-hydroxy-2-oxo-3H-1,3-benzothiazol-7-yl)ethylamino]propanesulphonamide hydrochloride a) 2-[2-(4-Chlorophenyl)ethoxy]acetic acid 2-(4-Chlorophenyl)ethanol (10 g) was stirred in 50% aqueous sodium hydroxide (70 ml), tetrabutylammoniumbromide (1.4 g) was added and the mixture stirred for 1 hour. t-Butylbromoacetate (28.6 ml) in toluene (140 ml) was added and stirring continued for 18 hours. Water (50 ml) was added and after 2 hours the mixture was cooled in ice and acidified to pH 1 with concentrated hydrochloric acid. The organic layer was separated and the aqueous extracted with ethyl acetate. The combined organic extracts were washed with brine and dried ($MgSO_4$). The solvent was removed in vacuo to give a pale yellow oil This was dissolved in dichoromethane (100 ml) and trifluoroacetic acid (100 ml) added, the mixture was heated at reflux for 1 hour. The volatiles were removed in vacuo and the residue taken up in sodium hydroxide and washed with ethyl acetate. The aqueous layer was then acidified with concentrated hydrochloric acid and extracted with ethyl acetate, this ethyl acetate was washed with water, dried ($MgSO_4$) and the volatiles removed in vacuo to provide the subtitle compound as a buff solid (16.4 g) which was used without further purification.

Mass spectrum EI 214/6 (M).

b) 2-[2-(4-Chlorophenyl))ethoxy]acetamide

The product from part a) (16.4 g) was dissolved in toluene (300 ml) and oxalyl chloride (13 ml) was added dropwise at room temperature and under nitrogen. The mixture was stirred for I hour and then dimethylformamide (0.3 ml) was added. After a further 2 hours the volatiles were removed in vacuo to provide a brown oil which was added dropwise to a stirred solution of concentrated ammonium hydroxide (60 ml). The solid which precipitated out was collected by filtration and washed with water and isohexane to yield the subtitle compound (6.6 g).

Mp. 106°–9° C.,
Mass spectrum FAB 214/6 (m+H);
$^1$H nmr (360 MHz, $CDCl_3$); 2.89 (2H, t), 3.73 (2H, t), 3.93 (2H,s), 5.87 (1H, brs), 6.22 (1H, brs), 7.16 (2H, d), 7.28 (2H,d).

c) 2-[2-(4-Chlorophenyl))ethoxy]ethanamine

The product from step b (6 g) was added portion wise to a stirred solution of boranetetrahydrofuran (1.0M in THF, 85 ml). The reaction was then heated at reflux under an inert atmosphere for 3 hours. The reaction was cooled and methanol (10 mls) was cautiously added. The solvents were removed in vacuo and the residue redissolved in methanol (100 ml) to which was added concentrated hydrochloric acid (sg. 1.18, 4 ml). This solution was heated at reflux for 30 minutes and then the solvent removed in vacuo. The residue was taken up into water and washed with ether. Sodium bicarbonate was added and the aqueous extracted with ethyl acetate. The ethyl acetate was washed with water, brine and dried ($MgSO_4$). The volatiles were removed in vacuo to provide the subtitle compound as a oil (5.5 g) which was used without further purification.

Mass spectrum EI 200/2 (M+H);

d) Methyl 3-[2-[2-(4-Chlorophenyl)ethoxy]ethylaminosulphonyl]propanoate

The product from part d (1.1 g) was stirred under nitrogen in dichloromethane (30 ml), triethylamine (1.52 ml) was added followed by methyl 3-(chlorosulphonyl)propanoate (2.04 g). The mixture was stirred groom temperature for 3 hours. The volatiles were removed in vacuo and the residue purified by flash chromatography over silica (60% ether/petrol) to provide the subtitle compound as an oil (1.1 g).

Mass spectrum FAB 350/2 (m+H);
$^1$H nmr (360 MHz, $CDCl_3$); 2.80 (2H, t), 2.82 (2H, t), 3.26 (2H, q), 3.33 (2H, t), 3.54 (2H, t), 3.67 (2H, t), 3.72 (3H, s), 4.63 (1H, t), 7.14 (2H, d), 7.27 (2H, d).

e) N-[2-[2-(4-Chlorophenyl)ethoxy]ethyl]-3-[2-(4-hydroxy-2-oxo-3H-1,3 -benzothiazol-7-yl)ethylamino]propanesulphonamide hydrochloride.

The product from part d (1.1 g) was dissolved in toluene (50 ml) under nitrogen and cooled to −78° C. Diisobutylaluminiumhydride (1.5M in toluene, 2.6 ml) was added dropwise and the mixture kept at −78° C. for 10 minutes. The reaction was quenched with 10% hydrochloric acid in methanol and the mixture allowed to warm to room temperature. The mixture was poured into 10% hydrochloric acid and extracted with ether. The combined organic extracts were washed with water then dried over magnesium sulphate and then about 70% of the solvent was removed in vacuo. Methanol (20 ml) was added to the mixture and again the about 70% of the solvent was removed in vacuo, this was repeated twice more. The solution was then diluted with methanol (20 ml) and 7-(2-aminoethyl)-4-hydroxy-1,3-benzothiazol-2(3H)-one hydrochloride (0.92 g) added. The pH was adjusted to pH 4 with glacial acetic acid. Sodium-cyanoborohydride (0.247 g) was added and the mixture stirred under nitrogen for 2 hours. The mixture was made basic by the addition of concentrated aqueous ammonium hydroxide solution. The volatiles were removed in vacuo and the residue purified by flash chromatography (2.5–10% methanol/dichloromethane). The material was further purified by reverse phase HPLC using 50% to 100% methanol in 0.1% aqueous trifluoroacetic acid as eluant to yield, after conversion to the hydrochloride salt, the title compound (0.089 g) as a white solid.

Mp. 190°–3°C.;
Mass spectrum: FAB 514/16 (M+H);
$^1$H nmr (360 MHz., $d_6$DMSO) 1.99 (2H, m), 2.82 (4H, m), 3.12 (8H, m), 3.45 (2H, t), 3.60 (2H, t), 6.76 (1H, d), 6.87 (1H, d), 7.30 (5H, m), 8.87 (2H, brs), 10.14 (1H, s), 11.77 (1H, brs);
Analysis Found: C, 46.68; H, 5.55; N, 7.47; S, 10.86%.
Required for $C_{22}H_{28}N_3O_5S_2$. HCl. $H_2O$; C,46.47; H, 5.50; N, 7.39; S, 11.28%.

EXAMPLE 6

3-[2-(4-Hydroxy-2-oxo-3H- 1,3-benzothiazol-7-yl)ethylamino]-N-[2-[2-(4-methylphenyl)ethoxy]ethyl]propanesulphonamide hydrochloride.

a) 2-[2-(4-Methylphenyl)ethoxyacetic acid 2-(4-Methylphenyl)ethanol(8.16 g) was stirred in 50% aqueous sodium hydroxide (25 ml). t-Butylbromoacetate (9.05 ml) in toluene (30 ml) was added together with tetrabutylammoniumbromide (2.2 g) and the mixture stirred for 18 hours. Iced water (100 ml) was added followed by ether, the organic layer was separated and then the aqueous layer acidified with hydrochloric acid. The acidified aqueous was extracted with ether and this extract was washed with brine, dried (MgSO$_4$). The solvent was removed in vacuo to give the subtitle compound as a white solid (1.1 g) which was used without further purification.

$^1$H nmr (360 MHz, CDCl$_3$); 2.32 (3H, s), 2.91 (2H, t), 3.77 (2H, t), 4.10 (2H, S), 7.11 (4H, m).

b) 2-[2-(4-Methylphenyl)ethoxy]acetamide

The subtitle compound (0.77 g) was prepared according to the procedure in example 1 part b using 2-[2-(4-methylphenyl)ethoxy]acetic acid (1.1 g). oxalyl chloride (1.44 g), concentrated ammonium hydroxide (20 ml), and toluene (40 ml).

mp 106°–7° C.;

Mass spectrum FAB 194 (M+H 100).

c) 2-[2-(4-Methylphenyl)ethoxy]ethanamine hydrochloride

The subtitle compound (6.25 g) was prepared according to the procedure in example 5 part c using 2-[2-(4-methylphenyl)ethoxy]acetamide (5.79 g), borane-tetrahydrofuran solution (1.0M in THF, 75 ml), and tetrahydrofuran (40 ml).

Mass spectrum FAB 180 (M+H, 100);

$^1$H nmr (360 MHz, CDCl$_3$); 2.30 (3H, s), 2.87 (2H, t), 3.17 (2H, d), 3.65–3.73 (4H, m), 7.11 (4H, m), 8.30 (2H, brs).

d) Methyl 3-[2-[2-(4-methylphenyl)ethoxy]ethylaminosulphonyl]propanoate

The subtitle compound (2.49 g) was prepared according to the procedure in example 5 part d using 2-[2-(4-methylphenyl)ethoxy]ethanamine hydrochloride (3.5 g) triethylamine 4.74 ml) methyl 3-(chlorosulphonyl)propanoate (3.08 g), and dichloromethane (80 ml).

Mass spectrum FAB 330 (M+H, 119 (100).

e) 3-[2-(4-hydroxy-2-oxo-3H-1,3-benzothiazol-7-yl)ethylamino]-N-[2-[2-(4-methylphenyl)ethoxy]ethyl]propanesulphonamide hydrochloride.

The title compound (0.2 g) was prepared according to the procedure in example 5 part e using methyl 3-[2-[2-(4-methylphenyl)ethoxy]ethylaminosulphonyl]propanoate (2.49 g), diisobutylaluminiumhydride (1.5M in toluene, 7.5 ml), 7-(2-aminoethyl)4-hydroxy-1,3-benzothiazol-2 (3H)-one hydrochloride (2.2 g) and sodium cyanoborohydride (0.48 g).

m.p. 213°–5° C.;

Mass spectrum FAB 494 (M+H);

$^1$H nmr (360 MHz., d$_6$DMSO) 1.99 (2H, m), 2.25 (3H, s), 2.74–2.84 (4H, m), 3.06 –3.15 (8H, m), 3.45 (2H, t), 3.57 (2H, t), 6.75 (1H, d), 6.87 (1H, d), 7.10 (4H, m), 7.30 (1H, t), 8.61 (2H, s), 10.11 (1H, s), 11.77 (1H, brs).

EXAMPLE 7

3-[2-(4Hydroxy-2-oxo-3H-1,3-benzothiazol-7-yl)ethylaminino]-N-[2-(2-phenyl - 1propoxy)ethyl]propanesulphonamide hydrochloride.

a) 2-(2-Phenyl-1-propoxy)acetic acid

The subtitle compound (14.95 g) was prepared according to the procedure in example 6 part a using 2-phenyl-1-propanol (13.6 g), t-butylbromoacetate (19.5 g), tetrabutylammoniumbromide (3.2 g), toluene (70 ml), 50% aqueous sodium hydroxide (25 ml).

$^1$H nmr (360 MHz, CDCl$_3$); 1.32 (3H, d), 3.08 (1H, m), 3.67 (2H, t), 4.07 (2H, S), 7.23–7.34 (5H, m).

b) 2-(2-Phenyl-1-propoxy)acetamide

The subtitle compound (4.39 g) was prepared according to the procedure in example 5 part b using 2-(2-phenyl-1-propoxy)acetic acid (5.0 g), oxalyl chloride 4.5 ml), concentrated ammonium hydroxide (20 ml), and toluene (30 ml).

Mass spectrum GC 134 (M-59);

$^1$H nmr (360 MHz, CDCl$_3$); 1.31 (3H, d), 3.05 (1H, m), 3.61 (2H, m), 3.90 (2H, q), 7.22 (3H, m), 7.33 (2H, m).

c) 2-(2-Phenyl-1-propoxy)ethanamine hydrochloride

The subtitle compound (3.58 g) was prepared according to the procedure in example 5 part c using 2-(2-phenyl-1-propoxy)acetamide (3.86 g), borane-tetrahydrofuran solution (1.0M in THF, 50 ml), and tetrahydrofuran (40 ml).

Mass spectrum GC 180 (M+H).

d) Methyl 3-[2-(2-phenyl-1-propoxy)ethylaminosulphonyl]propanoate

The subtitle compound (2.0 g) was prepared according to the procedure in example 5 part d using 2-(2-phenyl-1-propoxy)ethanamine hydrochloride (3.58 g), triethylamine (5.65 ml) methyl (3-chlorosulphonyl)propanoate (3.73 g), and dichloromethane (70 ml).

Mass spectrum GC 224 ( M-105);

$^1$H nmr (360 MHz, CDCl$_3$); 1.27 (3H, d), 2.75 (2H, t), 3.02 (1H, m), 3.20–3.29 (4H, m), 3.45–3.56 (4H, m), 3.72 (3H,s), 4.42 (1H,t), 7.21–7.34 (5H, m).

e) 3-[2-(4-Hydroxy-2-oxo-3H-1,3-benzothiazol-7-yl)ethylamino]-N-[2-(2-phenyl -propoxy)ethyl]propanesulphonamide hydrochloride.

The title compound (0.164 g) was prepared according to the procedure in example 5 part e using methyl 3-[2-(2-phenyl-1-propoxy)ethylaminosulphonyl]propanoate (1.01 g), diisobutylaluminiumhydride (1.5M in toluene, 3 ml), 7-(2-aminoethyl)-4-hydroxy-1,3-benzothiazol-2(3H)-one hydrochloride (0.89 g) and sodium cyanoborohydride (0.19 g).

m.p. 183°–4° C.;

Mass spectrum FAB 494 (M+H);

Analysis Found: C, 52.42; H, 6.31; N, 8.28; S, 11.74%. Required for C$_{23}$H$_{31}$N$_3$O$_5$S$_2$.HCl; C, 52.11; H, 6.08; N, 7.93; S, 12.10%.

EXAMPLE 8

3-[2-(4-Hydroxy-2-oxo-3H-1,3-benzothiazol-7-yl)ethylamino]-N-[2-[2-(2 -methylphenyl)ethooxy]ethyl]propanesulphonamide hydrochloride.

a) 2-[2-(2-Methylphenyl)ethoxy]acetic acid

The subtitle compound (8.91 g) was prepared according to the procedure in example 5 part a using 2-(2-methylphenyl)ethanol (5.0 g), t-butylbromoacetate (5.47 ml), tetrabutylammoniumbromide (0.78 g), toluene (80 ml), 50% aqueous sodium hydroxide (40 ml), trifluoroacetic acid (20 ml) and dichloromethane (20 ml).

$^1$H nmr (360 MHz, CDC$_3$); 2.34 (3H, s),2.97 (2H, t), 3.75 (2H, t), 4.13 (2H, S), 7.12–7.17 (4H, m) 8.14 (1H, brs).

b) 2-[2-(2-Methylphenyl)ethoxy]acetamide

The subtitle compound (5.02 g) was prepared according to the procedure in example 5 part b using 2-[2-(2-methylphenyl)ethoxy]acetic acid (6.726 g), oxalyl chloride (6.22 ml), concentrated ammonium hydroxide (60 ml), and toluene (60 ml).

Mass spectrum FAB 194 (M+H);

$^1$H nmr (360 MHz, CDCl$_3$); 2.22 (3H, S), 2.86 (2H, t), 3.60 (2H, t), 3.80 (2H, S),7.06–7.19 (4H, m), 7.25 (2H, brs).

c) 2-[2-(2-Methylphenyl)ethoxy]ethanamine hydrochloride.

The subtitle compound (5.4 g) was prepared according to the procedure in example 5 part c using 2-[2-(2- methylphenyl)ethoxy]acetamide (5.13 g), borane-tetrahydrofuran solution (1.0M in THF, 53.5 ml), and tetrahydrofuran (100 ml).

Mass spectrum FAB 180 (M$^+$+H).

d) Methyl 3-[2-[2-(2-methylphenyl)ethoxy]ethylaminosulphony]propanoate

The subtitle compound (5.4 g) was prepared according to the procedure in example 5 part c using 2-[2-(2-methylphenyl)ethoxy]ethanamine hydrochloride (5.4 g) triethylamine (8.73 ml) methyl 3-(chlorosulphonyl)propanoate (4.66 g), and dichloromethane (100 ml).

Mass spectrum FAB 330 (M+H);

$^1$H nmr (360 MHz, CDCl$_3$); 2.32 (3H, s), 2.71 (2H, t), 2.91 (2H, t), 3.24 (2H, t), 3.34 (2H, t), 3.53 (2H, m), 3.62 (2H, t), 3.70 (3H, s), 4.64 ( 1H, t), 7.14 (4H, m).

e) 3-[2-(4-Hydroxy-2-oxo-3H-1,3-benzothiazol-7-yl)ethylamino]-N-[2-[2 -(2-methylphenyl)ethoxy]ethyl]propanesulphonamide hydrochloride.

The product from part d (2.0 g) was dissolved in toluene (100 ml) under nitrogen and cooled to −78° C. Diisobutylaluminiumhydride (1.5M in toluene, 6.22 ml) was added dropwise and the mixture kept at −78° C. for 10 minutes. The reaction was quenched with ethyl acetate followed by a 10% aqueous sodium potassium tartrate solution. The mixture was warmed to room temperature and after stirring for one hour the mixture was extracted with toluene. The combined organic extracts were washed with water then dried over magnesium sulphate and then about 70% of the solvent was removed in vacuo. Methanol (50 ml) was added to the mixture and again about 70% of the solvent was removed in vacuo, this was repeated twice more. This solution was then diluted with methanol (50 ml) and 7-(2-aminoethyl)4-hydroxy-1,3-benzothiazol-2(3H)-one hydrochloride (1.8 g) added. The pH was adjusted to pH 4 with glacial acetic acid. Sodium cyanoborohydride (0.398 g) was added and the mixture was stirred under nitrogen for 18 hours. The mixture was made basic by the addition of concentrated aqueous ammonium hydroxide solution and the volatiles were then removed in vacuo. The residue was purified by flash chromatography over silica (1% methanol/dichloromethane). The material was further purified by reverse phase HPLC using 35%–85% methanol in 0.1% aqueous trifluoroacetic acid as eluant to yield, after conversion to the hydrochloride salt, the title compound (0.38 g) as a white solid.

m.p. 184°–7° C.;

Mass spectrum FAB 494 (M+H);

$^1$H nmr (360 MHz., d$_6$DMSO) 1.74–1.77 (2H, m), 1.99 (2H, t), 2.27 (3H, s), 2.79–2.85 (4H, m), 3.07–3.16 (6H, m), 3.45–3.48 (2H, m), 3.55–3.61 (2H, m), 6.74 (1H, d), 6.88 (1H, d), 7.08–7.17 (4H, m), 7.32 (1H, t), 8.81 (1H, s), 10.17 (1H, s), 11.77 (1H, brs).

EXAMPLE 9

3-[2-(4-Hydroxy-2-oxo-3H-1,3-benzothiazol-7-yl)-ethylamino]-N-[2-[2 -phenylthioethoxy)ethyl]propanesulphonamide hydrochloride.

a) t-Butyl 2-(2-phenylthioethoxy)acetate

2-Phenylthioethanol (6.1 g), t-butylbromoacetate (7.9 ml), tetrabutylammoniumbromide (1.3 g), toluene (80 ml), and 75% aqueous sodium hydroxide (40 ml) were stirred together for 72 hours. The organic layer was separated and the aqueous layer extracted with dichloromethane. The combined organics were washed with brine, dried (MgSO$_4$) and the solvent was removed in vacuo to provide the subtitle compound (12.07 g).

Mass spectrum FAB 269 (M+H).

b) 2-(2-Phenylthioethoxy)acetamide

The product from part a (12.07 g) was dissolved in dichoromethane (50 ml) and trifluoroacetic acid (50 ml) was added, the mixture was stirred for 2 hours. The volatiles were removed in vacuo and the residue taken up in aqueous sodium bicarbonate and washed with ether. The aqueous layer was then acidified with concentrated hydrochloric acid and extracted with ethyl acetate. The ethyl acetate was washed with brine, dried (MgSO$_4$) and the volatiles removed in vacuo. The residue was dissolved in toluene (50 ml) and oxalyl chloride (50 ml) was added dropwise at room temperature and under nitrogen. Dimethylformamide (0.3 ml) was added dropwise and the mixture was stirred for 45 minutes. Volatiles were removed and the crude acid chloride was added dropwise to a stirred solution of concentrated ammonium hydroxide (50 ml) at −10° C. The solid which precipitated out was collected by filtration and washed with water and ether to yield the subtitle compound (3.53 g).

Mass spectrum FAB 212 (M+H);

$^1$H nmr (360 MHz, CDCl$_3$); 3.13 (2H, t), 3.72 (2H, t), 3.95 (2H, s), 5.58 (1H, brs),6.56 (1H, brs), 7.20–7.39 (5H, m).

c) 2-(2-Phenylthioethoxy)ethanamine hydrochloride.

The subtitle compound as its hydrochloride salt (6.0 g) was prepared according to the procedure in example 5 part c using 2-(2-phenylthioethoxy)acetamide (5.5 g), boranetetrahydrofuran solution (1.0M in THF, 60 ml), and tetrahydrofuran (60 ml).

d) Methyl 3-[2-(2-phenylthioethoxy)ethylaminosulphonyl]propanoate

The subtitle compound (2.85 g) was prepared according to the procedure in example 5 part d using 2-(2-phenylthioethoxy)ethanamine hydrochloride (6 g), triethylamine (4 ml) methyl 3-(chlorosulphonyl)propanoate (5.8 g), and dichloromethane (50 ml).

Mass spectrum FAB 348 (M+105).

e) 3-[2-(4-Hydroxy-2-oxo-3H-1,3-benzothiazol-7-yl)ethylamino]-N-[2-(2-phenylthioethoxy)ethyl]propanesulphonamide hydrochloride.

The title compound (0.106 g) was prepared according to the procedure in example 8 part e using methyl 3-[2-(2-phenylthioethoxy)ethylaminosulphonyl]propanoate (1.4 g), diisobutylaluminiumhydride (1.5M in toluene, 3 ml), 7-(2-aminoethyl)-4-hydroxy-1,3 -benzothiazol-2(3H)-one hydrochloride (1.2 g) and sodium cyanoborohydride (0.3 g).

m.p. 193°–4° C.;

Mass spectrum FAB 512 (M+H);

$^1$H nmr 360 MHz., d$_6$DMSO) 2.06 (2H, m), 2.85 (2H, m), 3.08 (6H, m), 3.15 (4H, m) 3.46 (2H, t), 3.59 (2H, t), 6.76 (1H, d), 7.19 (1H, m), 7.31–7.36 (4H, m), 9.06 (2H, s)10.17 (1 H, s), 11.78 (1H, br).

Pharmacological Example

The binding affinities of compounds of the above Examples for the DA$_2$ receptor binding sites in bovine pituitary membranes were determined from the displacement of [$^3$H]-N-n-propylnorapomorphine and of [$^3$H]-spiperone in the absence or presence of nonhydrolysable GTP analogue respectively, D. R. Sibley, A. DeLean and I. Creese, Anterior Pituitary Dopamine Receptors, Demonstration of Interconvertible High and Low Affinity States of the D-2 Dopamine Receptor, J. Biol. Chem., 1982, 257(11), 6351–6361.

The DA$_2$-receptor activity was also demonstrated in a functional screen, the rabbit isolated ear artery, as described by Brown and O'Connor, Br. J. Pharmacol., 1981, 73, 189P.

β$_2$-adrenoreceptor activity was demonstrated in the isolated trachea of the guinea pig, as described by I. G. Dougall, D. Harper, D. M. Jackson, and P. Leff, Br. J. Pharmacol., 1991, 104, 1057.

$\alpha_1$-Receptor activity was determined in the rabbit isolated ear artery using the following method:

Rabbit isolated ear artery

Male NZW rabbits (2.5–3.0 kg) were killed by intravenous injection of pentobarbitone sodium (60 mg/kg). The ears were removed and the proximal portion of the middle ear artery exposed and cannulated using a polypropylene cannula (0.75 mm external diameter). After removal, the artery was cleared of adherent connective tissue and 6 rings, 5 mm wide, were prepared preserving the plane of the circular smooth muscle. Tissues were mounted on fine tungsten wire hooks (0.25 mm diameter) in 20 ml organ baths containing Krebs solution of the following composition (mM): NaCl 117.56; NaHCO$_3$ 25.00; KCl 5.36; NaH$_2$PO$_4$ 0.89; MgSO$_4$ 1.18; glucose 11.10 and CaCl$_2$ 2.55. Cocaine (30 $\mu$M) and propanolol (1 $\mu$M) were included in the Krebs solution to block neuronal uptake and $\beta$-receptors respectively. Ascorbate (100 $\mu$M) was also added to prevent catecholamine oxidation. This solution was maintained at 37° C. and continuously gassed with 95% O$_2$: 5% CO$_2$. The upper wire hook was attached to an Ormed force displacement transducer, the lower hook being attached to a stationary support in the bath. Changes in isometric force were recorded on Advance Bryans AB500 flat-bed recorders.

EXPERIMENTAL

General

At the beginning of each experiment, a force of 1.0 g was applied to each tissue. This force was reinstated two or three times during a stabilisation period of approximately 60 min. until it remained constant. At the same time as the force was reinstated the baths were washed out. Agonist concentration-effect, E/[A], curves were constructed by cumulative additions of agonist at 0.5 log$_{10}$ increments. Responses (contractions) were recorded as a percentage of the maximum response of the standard agonist.

Quantification of agonism

Phenylephrine has been adopted as the standard agonist. An E/[A] curve to phenylephrine was constructed first. The phenylephrine was then washed out and an E/[A] curve to the test compound was constructed. Responses of compounds that produced agonism were expressed as a percentage of the maximum response to phenylephrine. The value of the asymptote of the test compound curve relative to phenylephrine indicated the intrinsic activity of the compounds. (Phenylephrine was assumed to have an intrinsic activity of 1).

The p[A$_{50}$] value is a measure of agonist potency. It is the negative logarithm of the agonist concentration which produces a response that is half the maximum response. For compounds with intrinsic activities significantly less than 1, i.e. =<0.8, it is possible to calculate efficacy ($\tau$) values and affinity (pK$_A$) values using the comparative method of analysis. This analysis assumes that phenylephrine is acting as a fill agonist in this system and thus uses it to define the operational model parameters E$_m$ and n (ref Leff, et al., "Estimation of agonist affinity and efficacy by direct and operational model fitting.," J. Pharmacol. Methods., 1989, 23, 225–237). These parameters can then be utilised to perform a comparative analysis on the test compound to be made. Affinity is expressed as a pK$_A$ (the negative logarithm of the agonist concentration that occupies half of the receptors).

Quantification of antagonism

Compounds that did not demonstrate agonism were investigated as antagonists by incubating tissues with as high a concentration of the compound as possible and subsequently constructing phenylephrine curves E/[A] curves. The degree of rightward shift of these phenylephrine curves compared to the control phenylephrine curve allowed an estimation of the affinity of a test compound to be made. Such affinity estimates are shown as pA$_2$ values (negative logarithm of the concentration of antagonist that produces a 2-fold rightward displacement of the control E/[A] curve).

Confirmation of $\alpha_1$-mediated agonism

Prazosin has been adopted as the standard $\alpha_1$ antagonist. If a test compound showed agonism then, upon reaching the asymptote of the test compound E/[A] curve, prazosin (1 $\mu$M) was added to see if the response was reversed. If an $\alpha_1$ antagonist reverses the response of the test compound this suggests that the agonism is $\alpha_1$ mediated.

We claim:

1. A compound of formula I, including optical isomers thereof,

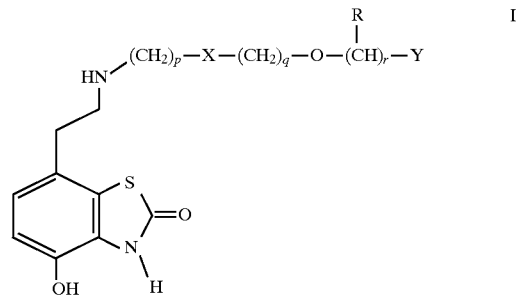

wherein

X represents —SO$_2$NH— or —NHSO$_2$—, p, q and r independently represent 2 or 3, Y represents thienyl optionally substituted by C$_1$–C$_6$ alkyl or halogen, or phenylthio- or phenyl optionally substituted by C$_1$–C$_6$ alkyl or halogen, and each R independently represents H or C$_1$–C$_6$ alkyl, and pharmaceutically acceptable salts thereof.

2. A compound as claimed in claim 1, wherein q is 2.

3. A compound as claimed in claim 1, wherein r is 2.

4. A compound as claimed in claim 1, wherein Y is phenyl substituted by methyl.

5. A compound as claimed in claim 1, wherein Y is phenyl substituted by a halogen substituent selected from a chloro- or fluoro-substituent.

6. A compound as claimed in claim 1, wherein X is SO$_2$NH, p is 3 and q and r are each 2.

7. A compound as claimed in claim 1, wherein X is NHSO$_2$, and p, q and r are all 2.

8. A compound as claimed in claim 1, in the form of a pharmaceutically acceptable salt selected from the hydrochloride, citrate, D,L-lactate, hemisulphate, hemitatrate, D-gluconate, methanesulphonate, p-toluenesulphonate, hemifumarate, benzoate, xinafoate, hemisuccinate, 3-hydroxy-2-naphthoate, hemiembonate, hemimaleate, D-camphorsulphonate, 10-undecanoate, mandelate, naphthalene-1-sulphonate, naphthalene-2- sulphonate, 4-methoxybenzoate, 4-chlorobenzoate, 5-methylsalicylate, saccharinate, monomethyl suberate, hemisuberate and diphenyl acetate salts.

9. A compound as claimed in claim 1, selected from
3-[2-(4-Hydroxy-2-oxo-3H-1,3-benzothiazol-7-yl) ethylamino]-N-[2-(2-phenylethoxy)ethyl] propanesulphonamide;
N-[2-[2-(4-Hydroxy-2-oxo-3H-1,3-benzothiazol-7-yl) ethylamino]ethyl]-2-(2-phenylethoxy) ethanesulphonamide;
3-[2-(4-Hydroxy-2-oxo-3H-1,3-benzothiazol-7-yl) ethylamino]-N-[2-[2-thienyl)ethoxy]ethyl] propanesulphonamide;
N-[2-[2-(4-Fluorophenyl)ethoxy]ethyl]-3-[2-(4-hydroxy-2-oxo-3H-1,3-benzothiazol-7-yl)ethylamino] propanesulphonamide;
N-[2-[2-(4-Chlorophenyl)ethoxy]ethyl]-3-(2-(4-hydroxy-2-oxo-3H-1,3-benzothiazol-7-yl)ethylamino] propanesulphonamide;
3-[2-(4-Hydroxy-2-oxo-3H-1,3-benzothiazol-7-yl) ethylamino]-N-[2-[2-(4-methylphenyl)ethoxy]ethyl] propanesulphonamide;
(R,S)-3-[2-(4-Hydroxy-2-oxo-3H-1,3-benzothiazol-7-yl) ethylamino]-N-[2-(2-phenyl-1-propoxy)ethyl] propanesulphonamide;
3-[2-(4-Hydroxy-2-oxo-3H-1,3-benzothiazol-7-yl) ethylamino]-N-[2-[2-(2-methylphenyl)ethoxy]ethyl] propanesulphonamide; and
3-[2-(4-Hydroxy-2-oxo-3H-1,3-benzothiazol-7-yl) ethylamino]-N-[2-(2-phenylthioethoxy)ethyl] propanesulphonamide.

10. A compound as claimed in claim 9, in the form of the hydrochloride salt.

11. A method for the production of a compound as claimed in claim 1, comprising selective reductive alkylation of a compound of formula II,

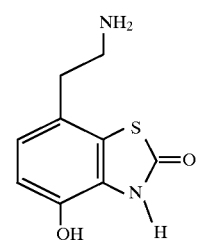

with a compound of formula III,

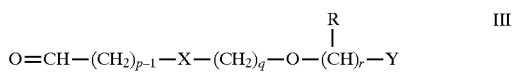

in which p, q, r, R, X and Y are as defined in claim 1, in the presence of a reducing agent.

12. A pharmaceutical composition comprising a compound of formula I as defined in claim 1, or a pharmaceutically acceptable salt, thereof, dispersed in a propellant optionally including excipients, lubricants or stabilising agents.

13. A pharmaceutical composition comprising a compound of formula I as defined in claim 1, or a pharmaceutically acceptable salt, thereof, in the form of a nebulised aqueous suspension or solution optionally with a pH and/or tonicity adjustment.

14. A pharmaceutical composition comprising a compound of formula I as defined in claim 1, or a pharmaceutically acceptable salt, thereof, in the form of a dry powder for inhalation, optionally including a pharmaceutically acceptable carrier.

* * * * *